United States Patent [19]
Holland et al.

[11] Patent Number: 5,902,831
[45] Date of Patent: May 11, 1999

[54] PREVENTION OF ATHEROSCLEROSIS USING NADPH OXIDASE INHIBITORS

[75] Inventors: James Arthur Holland, Bath; David K. Johnson, Genesco, both of N.Y.

[73] Assignee: The Research Foundation of State University of New York, Albany, N.Y.

[21] Appl. No.: 08/862,515

[22] Filed: May 23, 1997

Related U.S. Application Data

[63] Continuation-in-part of application No. 08/562,767, Nov. 27, 1995, Pat. No. 5,763,496.
[51] Int. Cl.⁶ ............................ A61K 31/12; A61K 31/11
[52] U.S. Cl. ........................ 514/685; 514/689; 514/699; 514/824
[58] Field of Search ..................... 514/685, 689, 514/699, 824

[56] References Cited

FOREIGN PATENT DOCUMENTS

| | | |
|---|---|---|
| 4109627 | 3/1991 | Germany . |
| 6135880 | 5/1994 | Japan . |
| 06145040 | 5/1994 | Japan . |
| 06227977 | 8/1994 | Japan . |
| 07165575 | 6/1995 | Japan . |
| 07179853 | 7/1995 | Japan . |
| WO9513063 | 5/1995 | WIPO . |

OTHER PUBLICATIONS

Miikki, V. et al., Characterization of the humic material formed by composting of domestic and industrial biowastes. Part 1 HPLC of the cupric oxide oxidation products from humic acids; Chemosphere 29(12), 2609–18 (1994).

van der Hage, Erik R.E. et al., Ammonia chemical ionization mass spectrometry of substituted phenylpropanoids and phenylalkyl phenyl ethers; J. Mass. Spectrom. 30(4), 541–8 (1995).

Senaratne et al. "Lovastatin prevents the impairment of endothelium dependent . . . " *Cardivasc. Res. 25*, 568–578 (1991).

Goldstein et al. "Regulation of low–density lipoprotein receptors: implications . . . " *Circulation 76*, 504–507 (1987).

Wasielewski "Lovastatin verzogert Athersklerose . . . " *A. Allg. Med. 68*, 987 (1993).

Aviram et al. "Lovastatin Inhibits Low–Density Lipoprotein Oxidation and Alters Its Fluidity . . . " *Metabolism 41*, 229–235 (1992).

Weber et al. "Antioxidants inhibit monocyte adhesion by suppressing nuclear . . . " *Arterioscler. Thromb. 14*, 1665–1673 (1994).

Bors et al. "Antioxidants: their function and mechanism as radical scavengers" *Proc. Int. Conf. Superoxide 1*, 38–43 (1982).

Keaney et al. "Atherosclerosis, Oxidative Stress, and Antioxidant Protection . . . " *Prog. Cardiovasc. Dis. 38*, 129–154 (1995).

Day et al. "Hypercholesterolemia and simvastatin therapy: Effects on cell membrane . . . " *Clin. Chem. 21*, S137 (1995).

Pschyrembel "Klinisches Worterbuch" 132 (1994).

*Primary Examiner*—Kimberly Jordan
*Attorney, Agent, or Firm*—Heslin & Rothenberg, P.C.

[57] ABSTRACT

A method for the prevention and treatment of atherosclerosis and its related diseases in mammals, in which an NADPH oxidase inhibitor is administered, is provided. The NADPH oxidase inhibitor prevents the production of reactive oxygen species upon exposure of endothelial cells to atherogenic LDL levels, thus resulting in decreased endocytosis and vascular hyperpermeability. Preferred NADPH oxidase inhibitors are of the formula:

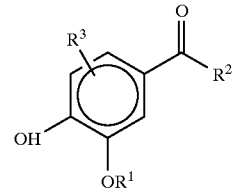

Additionally, there is provided a diagnostic method for predicting risk of a human patient to atherosclerotic-related diseases.

20 Claims, 4 Drawing Sheets

PREVENTION OF ATHEROSCLEROSIS USING NADPH OXIDASE INHIBITORS

CROSS-REFERENCE TO RELATED APPLICATION

This application is a continuation-in-part of U.S. patent application Ser. No. 08/562,767 filed Nov. 27, 1995, now U.S. Pat. No. 5,763,496.

STATEMENT AS TO RIGHTS UNDER FEDERALLY SPONSORED RESEARCH

This invention was made with support from the Department of Veterans Affairs (Merit Review 0002) and from the National Institutes of Health (Grant No. 5R01 HL49573). The United States government may have certain rights in the invention.

FIELD OF THE INVENTION

The present invention relates to therapeutic methods for the prevention and treatment of atherosclerosis and diseases resulting from endothelial hyperpermeability. More particularly, the present invention relates to the prevention and treatment of these diseases through the administration of an NADPH oxidase inhibitor.

BACKGROUND OF THE INVENTION

Atherosclerosis with its sequelae of heart attack, strokes, and peripheral vascular disease is the leading cause of death in the United States with over 800,000 deaths per year. Excluding accidents, suicides, and homicides, atherosclerotic-related diseases account for nearly 50% of all deaths. Epidemiologic studies show that a large percentage of those afflicted have an elevation in blood low density lipoprotein (LDL) levels. LDL carries cholesterol from the liver to body tissues. An elevated cholesterol level (hypercholesterolemia) is commonly associated with an elevation in LDL levels. High blood cholesterol levels, specifically LDL-cholesterol, increase risk for coronary heart disease (CHD), whereas lowering total cholesterol and LDL-cholesterol levels reduces CHD risk.

Many pharmaceutical agents have been developed to treat or prevent atherosclerosis and its complications by controlling abnormally high blood LDL levels or lowering cholesterol levels. The most widely known of these agents include nicotinic acid, clofibrate, dextrothyroxine sodium, neomycin, beta-sitosterol, probucol, cholestyramine and HMG-CoA reductase inhibitors, such as lovastatin and simvastatin. However, the usefulness of these agents is limited by the frequent occurrence of acute side effects. Such side effects may include intense cutaneous flush, pruritus, gastrointestinal irritation, hepatotoxicity, cardiac arrhythmias, nausea, weight gain, alopecia, impotence, abdominal pain, diarrhea, eosinophilia, skin rash, musculoskeletal pain, blurred vision, mild anemia, leukopenia, the enhancement of gallstones, constipation, and impaction. Moreover, there is only a partial correlation between lowering of serum cholesterol and the reduction of atherosclerosis. Not all patients with atherosclerotic disease have high cholesterol and not all patients with high cholesterol have atherosclerotic disease.

The pathobiology of atherosclerosis indicates a major role for vascular endothelial involvement. Perturbation of the endothelium, without overt death and loss of endothelial cells, with resultant change in endothelial permeability to various blood materials is an important feature in the development of atherosclerotic lesions. Materials contained in the blood subsequently pass through this endothelial tissue and accumulate in the intima of the arterial wall. Even a moderate increase in endothelial permeability (hyperpermeability) is accompanied by a significant increase in the incidence of atherosclerotic events.

One mechanism by which vascular hyperpermeability can occur in the presence of an intact endothelium is increased endothelial endocytosis due to perturbation of the endothelium. The endothelium can be perturbed by various conditions, including high levels of low density lipoprotein (LDL) in the bloodstream and shear stress, as occurs in hypertension. Diabetes mellitus and smoking can also give rise to perturbation of the endothelium. In studies in support of the instant invention, human vascular endothelial cells (EC) were exposed to high LDL concentrations (up to 330 mg/dL cholesterol) for prolonged periods. The results, as demonstrated by stability of cell count for instance, indicate that EC death and loss do not occur in humans during the promotion of atherosclerotic plaque formation by LDL. When endothelial hyperpermeability is referred to herein, the process is primarily one of increased transcytosis rather than loss of physical integrity of the cell membrane or separation between formerly adherent cells.

Initially, endothelial perturbation occurs, resulting in increased endocytosis and LDL accumulation in the subendothelial space. Thus, exposure to high LDL levels induces heightened EC endocytosis. Studies indicate that exposure to LDL, in concentration ranges that are considered from epidemiologic studies to be atherogenic (endothelial cells exposed to >140 mg/dL LDL cholesterol, for example), is necessary for exaggerated endocytosis. Another key finding is that once heightened endocytosis develops, it persists. Such a persistent change in EC functional state is consistent with the endothelial perturbation, or vascular hyperpermeability, concept.

Endocytosis is a fundamental, apparently ubiquitous, cellular event. During endocytosis, a segment of plasma membrane is interiorized to form a vesicle that migrates into the cytoplasm. This vesicle may participate in transcellular transport via transcytosis. The endocytosis regulatory mechanism is not well understood, but studies related to the instant invention demonstrate that reactive oxygen species, such as $H_2O_2$ and $O_2^-$, enhance EC endocytosis. Cells generate reactive oxygen species (ROS) as byproducts of normal cellular metabolism. Perturbed endothelial cells increase reactive oxygen species production via the activation of nicotinamide adenine dinucleotide phosphate (NADPH) oxidase.

NADPH oxidase is an enzyme that has been well characterized in leukocytes, but leukocyte-type NADPH oxidase has not been previously identified in endothelial cells. Studies undertaken in support of the instant application have demonstrated that it occurs in endothelial cells. Activation of NADPH oxidase results in the transfer of electrons from NADPH to oxygen, resulting in the generation of $O_{2-}$. The active form of the oxidase is a complex assembled from membrane-bound proteins that include cytochrome $b_{558}$ (composed of $gp91_{[phox]}$ and $p22_{[phox]}$) and cytosolic components, of which three have been characterized, $p47_{[phox]}$, $p67_{[phox]}$ and a low molecular weight GTP-binding protein. Cytochrome $b_{558}$ consists of a 22 kD polypeptide which tightly binds to a glycosylated 91 kD polypeptide.

It is known that inheritable abnormalities of the NADPH oxidase enzyme complex result in Chronic Granulomatous Disease (CGD), a congenital disorder in which leukocytes are unable to generate reactive oxygen species in response to microorganisms. Studies on CGD, in which NADPH oxidase activity is insufficient or absent, have shown that genetic variants of NADPH oxidase exist. There have been no studies, though, to identify NADPH oxidase genetic variants that produce excessive amounts of reactive oxygen species. If such variants exist and are common in our population, then people inheriting these genetic variants may be at higher risk of heart attack, stroke, and peripheral vascular disease.

The membrane-bound enzyme, NADPH oxidase, exists in an inactive form in quiescent cells. Upon cell perturbation, the enzyme complex assembles and is converted into an active state causing intensified reactive oxygen species generation (oxidative burst). Studies attempting to delineate the NADPH oxidase activation mechanism indicate that unsaturated fatty acids, most potently arachidonic acid, directly activate NADPH oxidase. To ascertain if arachidonic acid activates the NADPH oxidase found in endothelial cells, studies were carried out in which cells were directly exposed to increasing arachidonic acid concentrations and reactive oxygen species production was measured. For these studies, EC were incubated with 1 to 25 $\mu$M arachidonic acid and $H_2O_2$ production measured. It was shown that arachidonic acid both induces EC $H_2O_2$ generation and promotes heightened EC endocytosis.

One explanation for the correlation between high LDL and atherosclerosis based on the above information is that exposure to high levels of LDL's promote phospholipase $A_2$ activation. At an intracellular threshold level, cytosolic free arachidonic acid converts NADPH oxidase from a dormant to an active state.

Evidence from experiments conducted in support of the instant invention indicates that reactive oxygen species enhance endocytosis, a characteristic of atherosclerosis, and that NADPH oxidase is the major cellular source. Although NADPH oxidase inhibitors are claimed to be effective in treating inflammatory conditions, they have not been heretofore suggested to treat diseases such as atherosclerosis, whose initial phase is characterized by increased endocytosis and vascular hyperpermeability. For example, European patent application 551662 discloses the use of NADPH oxidase inhibitors to control acute and chronic inflammations of the airways, joints, and blood vessels. Such inflammations of the vessels include those arterioscleroses that are of inflammatory origin, but the EP application does not envision atherosclerosis, because the etiology of atherosclerosis (i.e., whether inflammatory or not) has not been established.

The use of 4-hydroxy-3-methoxyacetophenone (trivial name, apocynin) as an NADPH oxidase inhibitor is known, and it has been suggested to be of utility in treating inflammatory diseases. Apocynin is a natural phenol isolated from the root of the plant *Picrorhiza kurroa*, which grows in the Himalaya mountains. Extracts of *Picrorhiza kurroa* have been used in traditional medicine in Southeast Asia for the treatment of diseases connected with inflammation and for the treatment of a variety of conditions including liver and lung diseases, fever, skin lesions, worm infections, rheumatic disease, urinary disorders, heart failure, and snake and scorpion bites. A more recent reference [Engels et al. *FEBS Lett.*, 305, 254–56 (1992)] suggests that apocynin may also be useful in preventing thrombosis. However, neither apocynin nor any other NADPH oxidase inhibitor has been shown to prevent atherosclerosis or vascular hyperpermeability attributable to heightened EC endocytosis and high LDL concentrations.

A method that prevents and treats atherosclerosis and its associated diseases, that is effective in most patients, and that avoids patient-deterring side effects would represent a substantial advance toward eliminating a major cause of death in this country. A method employing a readily available medicament that has already been used in humans would present additional significant advantages in the prevention and treatment of atherosclerosis and related diseases. In addition, a diagnostic method for predicting an individual's potential risk of developing atherosclerosis is highly desirable.

SUMMARY OF THE INVENTION

The present invention relates to the surprising discovery of an effective method and composition for treating and preventing atherosclerosis in mammals. The present invention provides a method for the therapeutic use of an NADPH oxidase inhibitor, preferably apocynin, for the treatment and prevention of conditions resulting from endothelial hyperpermeability, such as atherosclerosis. Inhibition of NADPH oxidase activation in endothelial cells diminishes vascular hyperpermeability. Other conditions associated with vascular hyperpermeability can also be treated or prevented by administering an NADPH oxidase inhibitor such as apocynin.

In one aspect, the present invention relates to methods for preventing or treating a condition resulting from endothelial hyperpermeability. The method comprises administering to a mammal suffering from a condition resulting from endothelial hyperpermeability a therapeutically effective amount of an NADPH oxidase inhibitor or a metabolic precursor to an NADPH oxidase inhibitor. The NADPH oxidase inhibition that results from the method of the invention may be distinguished by several overlapping, but distinct, features: (1) the dose of NADPH oxidase inhibitor or precursor may be insufficient to lower serum LDL by more than 10%; (2) the NADPH oxidase inhibitor or precursor may have a lower $IC_{50}$ vs human NADPH oxidase than vs human HMG-CoA reductase; or (3) the NADPH oxidase inhibitor or precursor may effect statistically equivalent inhibition of human NADPH oxidase in the presence and absence of mevalonate.

In another aspect, the invention relates to a method of treating or preventing a condition resulting from endothelial hyper-permeability which comprises administering to a mammal a therapeutically effective amount of a substance which inhibits $p47_{[phox]}$ translocation to the $gp91_{[phox]}$ and $p22_{[phox]}$ membrane bound NADPH oxidase components.

In a preferred aspect of the invention, the NADPH oxidase inhibitor is a compound of the formula:

wherein $R^1$, $R^2$ and $R^3$ are independently chosen from the group consisting of H, alkyl, cycloalkyl, heterocycloalkyl, alkenyl, alkynyl, aryl, heteroaryl, arylalkyl, heteroarylalkyl and substituted alkyl, cycloalkyl, heterocycloalkyl, alkenyl and alkynyl.

In another preferred aspect of the invention, the NADPH oxidase inhibitor is of the formula:

or a tautomer thereof, wherein $R^1$, $R^2$ and $R^3$ are independently chosen from the group consisting of H, alkyl, cycloalkyl, heterocycloalkyl, alkenyl, alkynyl, aryl, heteroaryl, arylalkyl, heteroarylalkyl and substituted alkyl, cycloalkyl, heterocycloalkyl, alkenyl and alkynyl.

In a more preferred aspect of the invention, the NADPH oxidase inhibitor is of the formula I, II or III, wherein $R^1$ and $R^2$ are each methyl and $R^3$ is H.

Compounds of the formula I are widely available commercially. Those that are not commercially available can be conveniently prepared by Friedel-Crafts acylation of the appropriate phenol or protected phenol, by aryllithium addition of a protected phenol to the appropriate carboxylic acid or arylcadmium addition to an acid chloride, followed by deprotection, as well as by any of the other well-known methods for forming ketones.

Other compounds of the genus II may be made in analogous fashion by oxidative dimerization of the appropriate phenol. All of these compounds are readily and reversibly oxidized to the quinoid structures by oxidation using any convenient oxidant such as hydrogen peroxide.

Conditions that result from vascular hyperpermeability include atherosclerosis and diseases related to atherosclerosis, including heart attack, stroke, and peripheral vascular disease. Compounds of formula I, II or III are especially well suited for treating and preventing atherosclerosis. By the terms "preventing" and "treating" applicant does not intend that the disease or condition must be completely abolished, only that there is some amelioration, i.e. that its normal course be substantially diminished, so that an improvement over the expected symptomology is clinically observable.

In another aspect, the present invention relates to a method for predicting the risk of a human patient to diseases, such as atherosclerosis, that result from endothelial hyperpermeability. The method comprises identifying a patient having elevated NADPH oxidase activity. Elevated NADPH oxidase activity is defined for the purpose of the present invention as more than 10% above the range found in paired controls. Such identification is preferably done by measuring the NADPH oxidase activity in white blood cells (polymorphonuclear leukocytes) of the patient. Polymorphonuclear leukocyte (PMN) NADPH oxidase activity may be measured using flow cytometry with 2,7-dichlorofluorescein diacetate as the indicator. After identifying such a patient, administration of an NADPH oxidase inhibitor, such as apocynin, can be recommended for preventing or treating atherosclerosis and its related diseases.

In each aspect of the invention, administering an NADPH oxidase inhibitor is intended to encompass the administration of compounds which are themselves NADPH oxidase inhibitors, as well as compounds that are metabolic precursors thereto (i.e., prodrugs). The operative feature is the inhibition of NADPH oxidase as a result of the administration of the compound in question.

DEFINITIONS

The following terms have the indicated meaning throughout:

"Alkyl" is intended to include linear, branched or cyclic hydrocarbon structures and combinations thereof. "Lower alkyl" means alkyl groups of from 1 to 8 carbon atoms. Examples of lower alkyl groups include methyl, ethyl, propyl, isopropyl, butyl, sand t-butyl, pentyl, hexyl, octyl, cyclopropylethyl, bornyl and the like. Preferred alkyl groups are those of $C_{20}$ or below.

"Cycloalkyl" is a subset of alkyl and includes cyclic hydrocarbon groups of from 3 to 8 carbon atoms. Examples of lower cycloalkyl groups include c-propyl, c-butyl, c-pentyl, norbornyl and the like.

"Heterocycloalkyl" means a cycloalkyl where one to two of the methylene ($CH_2$) groups is replaced by a heteroatom such as ), NR (wherein R is H or alkyl), S or the like. Examples of heterocycloalkyl include tetrahydrofuranyl, piperidine, dioxanyl and the like.

"Alkenyl" includes $C_{2-8}$ unsaturated hydrocarbons of a linear, branched or cyclic ($C_{5-6}$) configuration and combinations thereof. Examples of alkenyl groups include vinyl, allyl, isopropenyl, pentenyl, hexenyl, c-hexenyl, 1-propenyl, 2-butenyl, 2-methyl-2-butenyl and the like.

"Alkynyl" includes $C_{2-8}$ hydrocarbons of a linear or branched configuration and combinations thereof containing at least one carbon-carbon triple bond. Examples of alkynyl groups include ethyne, propyne, butyne, pentyne, 3-methyl-1-butyne, 3,3-dimethyl-1-butyne and the like.

"Aryl" and "heteroaryl" include a 5- or 6-membered aromatic or heteroaromatic ring containing 0–3 heteroatoms selected from O, N and S; a bicyclic 9- or 10-membered aromatic or heteroaromatic ring system containing 0–3 heteroatoms selected from O, N and S; or a tricyclic 13- or 14-membered aromatic or heteroaromatic ring system containing 0–3 heteroatoms selected from O, N and S; each of which rings is optionally substituted with 1–3 lower alkyl, substituted alkyl, substituted alkynyl, =O, —$NO_2$, halogen, hydroxy, alkoxy, —$OCH(COOH)_2$, cyano, —$NR^4R^4$ (wherein $R^4$ is independently H, lower alkyl or cycloalkyl, and —$R^4R^4$ may be fused to form a cyclic ring with N), acylamino, phenyl, benzyl, phenoxy, benzyloxy, heteroaryl or heteroaryloxy; each of said phenyl, benzyl, phenoxy, benzyloxy, heteroaryl and heteroaryloxy is optionally substituted with 1–3 substituents selected from lower alkyl, alkenyl, alkynyl, halogen, hydroxy, alkoxy, cyano, phenyl, benzyl, benzyloxy, carboxamido, heteroaryl, heteroaryloxy, —$NO_2$ and —$NR^4R^4$. The aromatic 6- to 14-membered carbocyclic rings include, e.g., benzene, naphthalene, indane, tetralin and fluorene, and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Alkoxy" refers to groups of from 1 to 8 carbon atoms of straight, branched or cyclic configuration and combinations thereof. Examples include methoxy, ethoxy, propoxy, isopropoxy, cyclopropyloxy, cyclohexyloxy and the like. "Acylamino" refers to groups of from 1 to 8 carbon atoms of a straight, branched or cyclic configuration and combinations thereof. Examples include acetylamino, butylamino, cyclohexylamino and the like.

"Halogen" includes F, Cl, Br and I.

"Arylalkyl" refers to an alkyl residue attached to an aryl ring. Examples include, e.g., benzyl, phenethyl and the like.

"Heteroarylalkyl" refers to an alkyl residue attached to a heteroaryl ring. Examples include, e.g., pyridinylmethyl, pyrimidinylethyl and the like.

"Substituted" alkyl, cycloalkyl, heterocycloalkyl, alkenyl or alkynyl refers to alkyl, cycloalkyl, heterocycloalkyl, alkenyl or alkynyl wherein up to three H atoms on each C atom therein are replaced with halogen, hydroxy, loweralkoxy, carboxy, carboalkoxy, carboxamido, cyano, carbonyl, $-NO_2$, $NR^5R^5$ (wherein $R^5$ is H, alkyl or arylalkyl), alkylthio, sulfoxide, sulfone, acylamino, amidino, phenyl, benzyl, heteroaryl, phenoxy, benzyloxy, heteroaryloxy and substituted phenyl, benzyl, heteroaryl, phenoxy, benzyloxy or heteroaryloxy.

BRIEF DESCRIPTION OF THE DRAWINGS

These and other objects, features and advantages of the invention will be evident from the following detailed description when read in conjunction with the accompanying drawings in which.

DETAILED DESCRIPTION OF THE INVENTION

The present invention provides a method for preventing and treating atherosclerosis and diseases related thereto, conditions associated with increased endothelial permeability. According to the invention, the administration of an NADPH oxidase inhibitor, such as apocynin, inhibits NADPH oxidase activation in endothelial cells. The activation of NADPH oxidase is the major cellular source of the oxidative burst (an intensified generation of reactive oxygen species), which is associated with serum LDL levels that are known to be atherogenic. The oxidative burst enhances endocytosis and endothelial hyperpermeability.

The present invention additionally provides a diagnostic method for predicting the risk of atherosclerosis-related diseases by measuring NADPH oxidase activity. Individuals with a clinically documented history of atherosclerotic-related diseases, or strong family history thereof, have higher NADPH oxidase activity than people without any medical or family history of the diseases.

Figure 7:
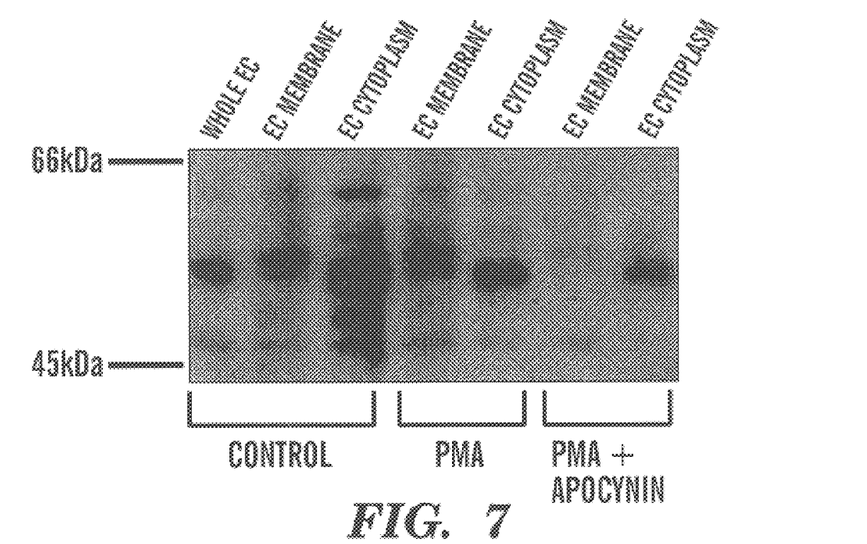
FIG. 7 is a printed reproduction of a Western-blot of the cytosolic and membrane fractions from control endothelial cells, PMA-exposed endothelial cells and PMA-exposed endothelial cells treated with 100 $\mu$g/ml apocynin showing the absence of p47$_{[phox]}$ in the membrane fraction.

A preferred NADPH oxidase inhibitor according to a method of the present invention is apocynin. Apocynin is an orthomethoxy-substituted catechol that acts to block NADPH oxidase complex assembly by inhibiting the translocation of the p47$_{[phox]}$ cytosolic oxidase subunit to the membrane fraction. Studies were performed in which EC were exposed to 10 nM PMA in the presence and absence of 100 $\mu$g/ml apocynin for 15 minutes. Subsequently, EC cytosolic and membrane fractions were isolated. Western-blot analysis of the fractions was performed using the monoclonal antibody against P47$_{[phox]}$. FIG. 7 reveals the absence of the cytosolic subunit p47$_{[phox]}$ in the membrane fraction of EC treated with apocynin.

While a preferred NADPH oxidase inhibitor in the present invention is apocynin, the method of the invention is not limited to apocynin, and a variety of other chemicals known to inhibit NADPH oxidase in endothelial cells may be used, as will be obvious to those skilled in the art. In the case of apocynin, the intact molecule (the ortho-methoxy phenol) appears to be effective as an inhibitor, and in addition, a dimer arising from metabolic oxidation is also highly effective and indeed may be the active species. Thus, compounds having an electron distribution similar to that in the dimer are effective inhibitors of NADPH oxidase and are contemplated within the invention. Examples of other types of NADPH oxidase inhibitors that may be useful include, but are not limited to, isoprenylation inhibitors such as lovastatin and compactin (see U.S. Pat. No. 5,224,916), benzofuranyl- and benzothenylthioalkane carboxylates (see EP application 551,662), and cytochrome b$_{558}$ fragments and their analogs (see PCT application WO 91/17763).

While it is believed that many of the known NADPH oxidase inhibitors act by interfering with the assembly of the active complex, the term NADPH oxidase inhibitor, as used herein, is not intended to be restricted as to mechanism. Any substance that inhibits the NADPH oxidase-catalyzed generation of reactive oxygen species is encompassed by the term "NADPH oxidase inhibitor". The claimed method for treating atherosclerosis by NADPH oxidase inhibitors can be distinguished from the known methods for treating atherosclerosis (although the mechanism was previously unknown) employing compounds that happen also to be NADPH inhibitors. The claimed method can employ doses of known inhibitors (e.g. lovastatin) that would be therapeutically ineffective to reduce LDL-cholesterol, i.e. that produce a less than 10% lowering of serum LDL-cholesterol.

Alternatively, the claimed method employs inhibitors that are targeted to the NADPH oxidase complex in that they have a lower IC$_{50}$ vs human NADPH oxidase than vs human HMG-CoA reductase. For the purpose of the present invention, the $IC_{50}$ is defined, according to standard practice, as the concentration of inhibitor required to inhibit the enzyme in question by 50%. The $IC_{50}$ vs human NADPH oxidase is measured as described in U.S. Pat. No. 5,244,916 column 11–12; the $IC_{50}$ vs human HMG-CoA reductase is measured as described by Edwards et al. [*J. Lipid Res.* 20, 4046 (1979)]. A brief description of the HMG-CoA reductase measurement is as follows:

A fragment of human liver is homogenized at 4° C. in 25 mL of buffer A (0.1 M sucrose, 0.05 M KCl, 0.04 M potassium phosphate and 0.03M potassium EDTA; pH 7.2) and the microsomes are prepared as described by Edwards and Gould [*J. Biol. Chem.* 247, 1520–1524 (1972)]. The microsomes are resuspended in buffer A to a concentration of approximately 82 mg protein/mL, solid DTT is added to a final concentration of 10 mM and the microsomes are homogenized. Three mL aliquots of the microsome suspension are frozen in glass tubes at a rate of 6–80° C. per min as described by Heller and Gould [*Biochem. Biophys. Res. Comm.* 50, 859–865 (1973)], and stored at −20° C. for up to two months.

For optimal solubilization of the reductase, the frozen microsomes are allowed to thaw at room temperature before addition of an equal volume of 50% glycerol in buffer B (buffer A plus 10 mM DTT) preheated to 37° C. The suspension is rehomogenized and then incubated at 37° C. for 60 minutes. The suspension is diluted threefold with buffer B preheated to 37° C. to a final glycerol concentration of 8.3%, rehomogenized and centrifuged at 100,000 g for 60 minutes at 25° C. The supernatant, containing solubilized HMG-CoA reductase, is removed and used immediately.

The activity of the solubilized HMG-CoA reductase is determined at 37° C. in a total volume of 0.5 mL using a spectrophotometer. The cell path length is 1.0 cm. The rate of oxidation of NADPH is initially determined in the absence of HMG-CoA and this blank value, if any, is subtracted from the rate obtained with both substrates.

Maximum activity is obtained by assaying the enzyme in buffer C (0.2M KCl, 0.16M potassium phosphate, 0.004 MEDTA, and 0.01 MDTT, pH 6.8) together with 0.2 mM NADPH and 0.1 mM RS-HMG-CoA. One unit of enzyme activity is defined as the amount required to oxidize 2 nmol NADPH per minute. Hence, one unit is equivalent to the synthesis of 1 nmol mevalonate per minute.

Inhibition is measured in buffer C. The results are expressed as the 50% inhibitory concentration ($IC_{50}$) for the test substance. Six to ten test substance concentrations, separated by approximately ½log, are tested in duplicate. The test substances are dissolved in buffer C for addition to the incubations. The $IC_{50}$ is calculated by linear interpolation.

A class of inhibitors that inhibits NADPH oxidase but does not block isoprenylation can be distinguished by the fact that they effect statistically equivalent inhibition of human NADPH oxidase in the presence and absence of mevalonate (see U.S. Pat. No. 5,244,916, column 14, line 60 to column 15, line 30).

In Vitro Apocynin Experiments

Experiments were performed in vitro using a high LDL endothelial cell tissue culture system. Endothelial cells were isolated from human umbilical cord veins and placed in experimental wells to which LDL media were added. The tissue culture components and chemicals are commercially available and were obtained from Sigma, Worthington, and Gibco. LDL was isolated from human blood plasma. Apocynin is available from Carl Roth GmbH (Germany).

Figure 1:
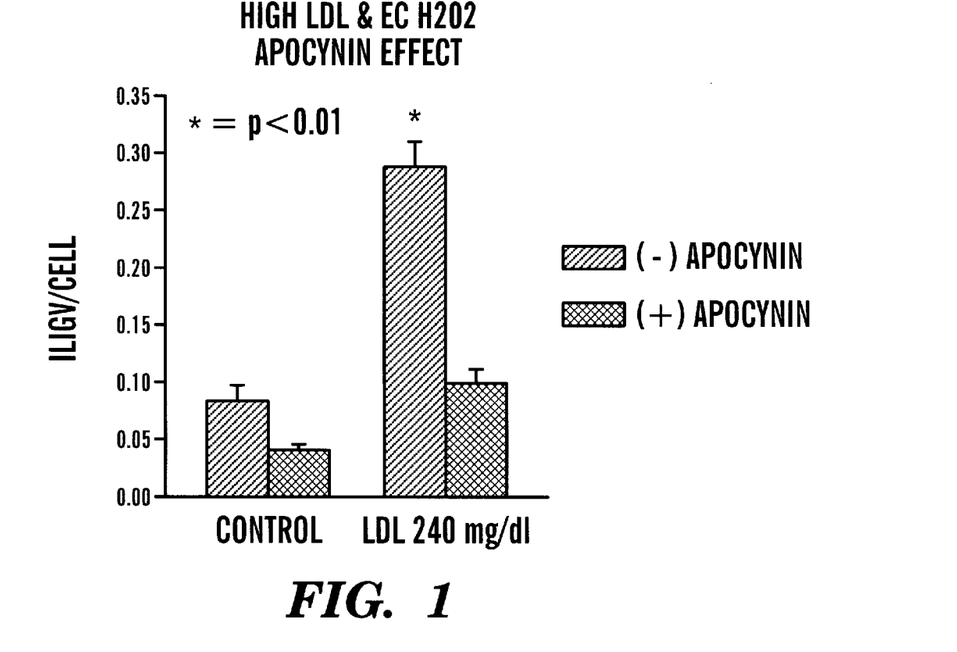
FIG. 1 is a graph of optical density from fluorescence spectroscopy, measured as "ILIGV", per cell for four test groups of endothelial cells, showing the effect of apocynin on high-LDL induction of endothelial cell peroxide production.
Figure 2:
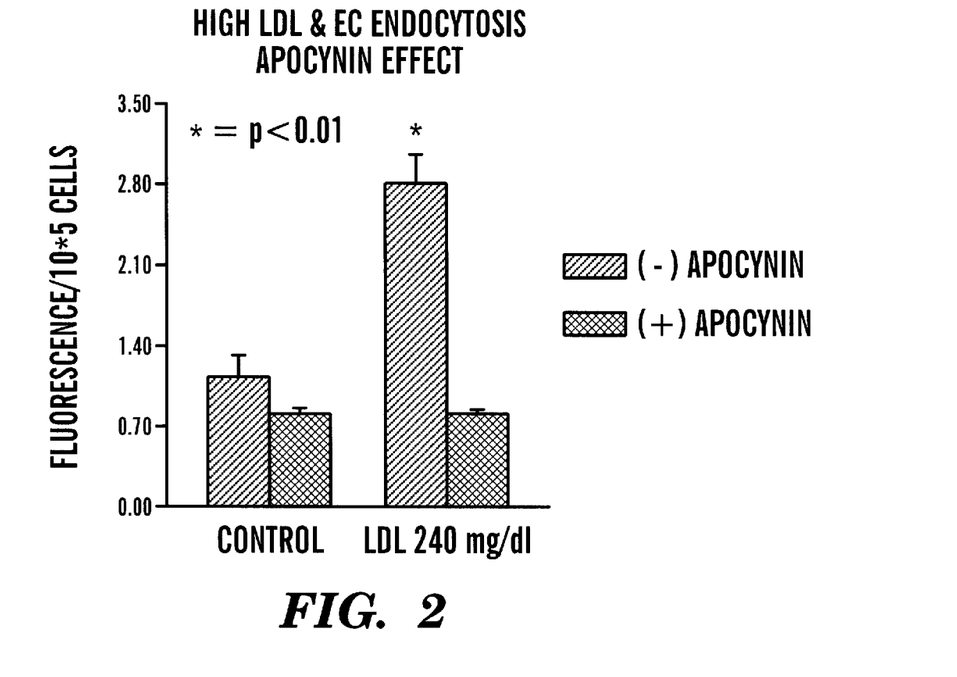
FIG. 2 is a graph of fluorescence per $10^5$ cells for four test groups of endothelial cells, showing the effect of apocynin on high-LDL induction of endothelial cell endocytosis.

Studies were conducted using apocynin to block NADPH oxidase activation and thereby prevent heightened endocytosis. Apocynin interferes with the assembly of a functional NADPH oxidase enzyme complex. For apocynin studies, EC were incubated with 240 mg/dL LDL cholesterol in the presence and absence of 100 μg/mL apocynin. As shown in FIGS. 1 and 2, apocynin effectively inhibits (1) the induction of $H_2O_2$ production and (2) endocytosis alterations associated with high concentrations of LDL.

As mentioned above, arachidonic acid activates EC NADPH oxidase directly, by inducing EC $H_2O_2$ generation; exposure to arachidonic acid promotes heightened EC endocytosis.

Figure 3:
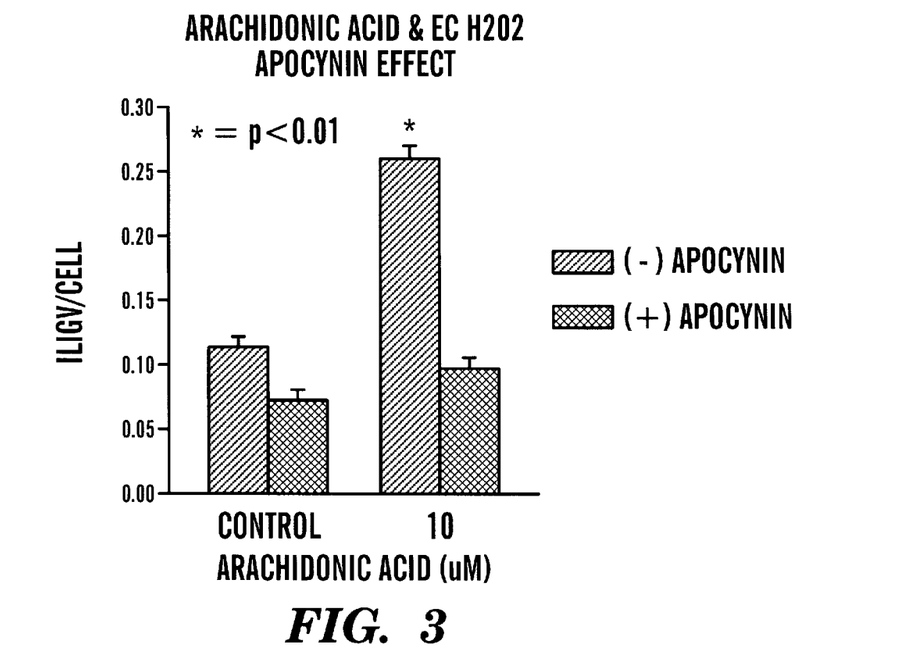
FIG. 3 is a graph of optical density from fluorescence spectroscopy, measured as "ILIGV", per cell for four test groups of endothelial cells, showing the effect of apocynin on arachidonic acid induction of endothelial cell peroxide production.

Further support that the arachidonic acid-induced oxidative burst results from NADPH oxidase activation is provided from the results of the following test in which apocynin was used to block NADPH oxidase activation. EC were incubated with 10 μM arachidonic acid in the presence and absence of 100 μg/mL apocynin. FIG. 3 shows that apocynin markedly reduces arachidonic acid-induced EC $H_2O_2$ generation.

It has been demonstrated that there is a lag time of approximately two minutes before apocynin acts to inhibit NADPH oxidase activity. This delay results from the time required for apocynin to be metabolized to an active product in a chemical reaction involving ROS and peroxidase. Following this delay in effect, cellular ROS production is nearly completely inhibited.

Figure 8:
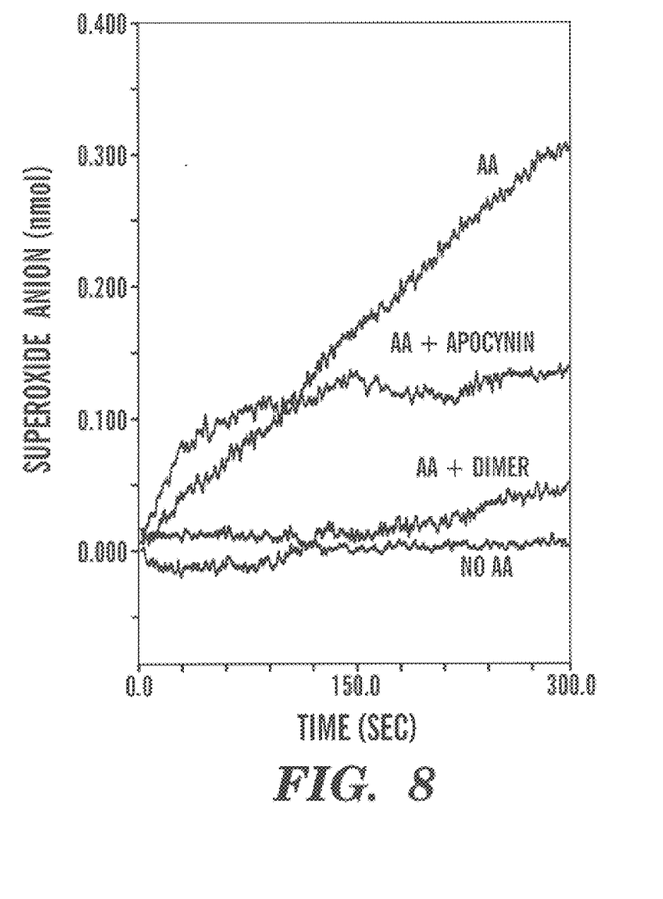
FIG. 8 is a graph showing $O_2$ generation by whole cell endothelial cell sonicate in response to arachidonic acid, in the presence and absence of apocynin and purified apocynin dimer.

The active metabolite of apocynin has been identified as a dimer possessing a quinone-like structure which arises from metabolic oxidation. Studies were performed to examine ROS generation by whole cell EC sonicate, in response to arachidonic acid, in the presence and absence of the purified apocynin dimer. As seen in FIG. 8, there was no lag time for the nearly complete inhibition of ROS generation in the presence of the purified apocynin dimer.

Synthesis and Isolation of Apocynin Dimer

I. Synthesis

A 0.02 mg/ml aqueous solution of apocynin is prepared by dissolving 10 mg apocynin volumetrically in 500 mL distilled $H_2O$. The final molarity of the solution is $1.2 \times 10^{-4}$M. A 3% $H_2O_2$ (m/m) solution is prepared by diluting 1 mL of 30% $H_2O_2$ (m/m, 9.8M) to 10 mL volumetrically with distilled $H_2O$. The final molarity of the solution is 0.98M. A 0.1 mg/mL solution of horseradish peroxidase (HRP) is prepared by dissolving 5 mg of solid HRP in 50 mL distilled $H_2O$ volumetrically.

100 mL of 0.02 mg/mL apocynin solution is combined with 100 μL (delivered via micropipette) of 0.1 mg/mL HRP solution in a clean, dried 250 mL erlenmeyer flask. A magnetic stir bar is added and the solution is stirred gently. The reaction is initiated by the addition of 24 μL (delivered via micropipette) of the 3% $H_2O_2$ solution. After 10 seconds, the reaction mixture is quenched by the addition of 1.5 mL of 0.1M $Na_2S_2O_3$. The solution is then allowed to stir vigorously for 2 minutes, at the end of which the pH of the solution is reduced to 3 to 4 by the addition of 5 drops 3M $H_2SO_4$.

The quenched reaction mixture is then divided into two 50 mL portions. Each portion is extracted twice with diethyl ether (2×15 mL) and the ether layers are combined. The combined ether extracts are dried for 10 minutes over a minimal amount of anhydrous $MgSO_4$, and then gravity filtered. The ether is removed by rotary evaporation, and the resulting product, primarily a mixture of apocynin and apocynin dimer, is dissolved in $CDCl_3$ for analysis by $^1$H-NMR Spectroscopy.

II. Isolation

After analysis by $^1$H-NMR, $CDCl_3$ is removed by rotary evaporation, and the crude product mixture is dissolved in a minimal volume of HPLC Grade methanol (<1 mL). If suspended particles exist, a nylon membrane syringe filter is used to filter the solution prior to injection onto the HPLC column. To isolate the dimer, reverse phase (C18) HPLC equipped with a UV detector is employed in a preparatory manner. The mobile phase is 50:50 methanol:acetate buffer (pH=4) and a 260 nm wavelength is used for detection.

Methanol is removed from the collected preparatory solution containing the dimer (10 to 20 mL) by rotary evaporation (approximately 1 hour).

A solid phase extraction filter cartridge (Alltech C18 500 mg—3 mL) is then prepared by pulling 10 mL HPLC Grade methanol, followed by 10 mL distilled $H_2O$ through the filter. The stripped preparatory solution is passed through the filter, followed by a 4 mL distilled $H_2O$ rinse. The filter is allowed to dry for approximately 10 minutes, then HPLC Grade methanol aliquots are pushed through the column and collected (5×5 mL). The methanol is removed by rotary evaporation, and the isolated dimer is dissolved in 3 mL $CDCl_3$. The dimer is then analyzed by $^1$H-NMR spectroscopy.

REDOX REACTION FOR APOCYNIN DIMER

While applicant does not wish to be limited by the hypothesis, it appears that apocynin may be a metabolic precursor of the species that actively inhibits NADPH oxidase.

Additional studies were conducted to provide further insight into the mechanism of NADPH oxidase activation. The cellular enzyme, phospholipase $A_2$ ($PLA_2$) hydrolyses membrane phospholipids releasing arachidonic acid intracellularly. $PLA_2$ inhibition by its antagonist, p-bromophenacyl bromide (BPB), suppresses the rise in cytosolic free arachidonic acid and limits this secondary messenger for NADPH oxidase activation. Thus, $PLA_2$ inhibition blocks LDL-EC NADPH oxidase activation. In these studies, EC were exposed to 240 mg/dL LDL-cholesterol with and without 10 μM BPB. BPB markedly diminished LDL-EC reactive oxygen species production.

$PLA_2$ is a $Ca^{2+}$-dependent enzyme. Likewise, $Ca^{2+}$ is required for NADPH oxidase activation in intact cells. $PLA_2$-mediated arachidonic acid release parallels extracellular $Ca^{2+}$ concentration. Studies were conducted to determine whether LDL-EC have increased cellular $Ca^{2+}$ influx. In these studies, EC were incubated with increasing LDL levels (30 to 240 mg/dL cholesterol), and cellular $Ca^{2+}$ influx was measured employing a $^{45}Ca^{2+}$ uptake assay as described by Lewis et al. [J. Clin. Invest., 82, 2045–2055 (1988)]. It was found that LDL-EC promote a dose-dependent rise in cellular $Ca^{2+}$ influx. LDL may induce $Ca^{2+}$ influx by EC exposure to $H_2O_2$, causing cellular permeabilization to $Ca^{2+}$ and resulting in an intracellular calcium elevation.

The above studies in vitro demonstrated that atherogenic LDL levels induce heightened EC endocytosis and that reactive oxygen species, produced predominantly by NADPH oxidase, mediate heightened EC endocytosis. To restate, while not intending to be held to any particular theory, one may hypothesize, based on the above studies in vitro, that reactive oxygen species, generated by activated EC NADPH oxidase, mediate hypercholesterolemia-induced vascular hyperpermeability via heightened EC endocytosis.

High LDL exposure initially activates phospholipase $A_2$ activity releasing arachidonic acid from phospholipids. Cytoplasmic free arachidonic acid, at a threshold level, converts an inactive genetic variant of NADPH oxidase to its active form. This genetic NADPH oxidase variant generates increased amounts of reactive oxygen species which perturb the cell membrane and enhance $PLA_2$ activation. $PLA_2$ activation is further enhanced by reactive oxygen species-mediated cellular $Ca^{2+}$ influx. Arachidonic acid released from membrane phospholipids markedly escalates NADPH oxidase enzyme complex recruitment and assembly. The multiple, membrane-bound, assembled enzyme complexes generate excessive quantities of reactive oxygen species, $O_2^-$ and $H_2O_2$. These reactive oxygen species increase membrane fluidity and decrease the energy of activation for endocytosis. The combination of these LDL-induced cellular events result in heightened EC endocytosis, vascular hyperpermeability, and increased transcellular transport via transcytosis.

Thus, inhibition of NADPH oxidase activation with apocynin, for example, prevents heightened EC endocytosis and reduces vascular hyperpermeability.

While not wishing to be restricted to a particular theory, it is possible that the inhibition of NADPH oxidase by the apocynin dimer may involve the disruption of the electron transport chain in the NADPH oxidase activation process. NADPH Oxidase activation requires the coupling of electron transport function between ubiquinone (co-enzyme Q) and cytochrome b. An oxidized dimer having a lower reduction potential than ubiquinone would then block the electron transport chain.

In Vivo Apocynin Experiments

To test the foregoing hypothesis, studies were conducted in vivo, which focused on the effect of NADPH oxidase inhibition on vascular hyperpermeability using a hypercholesterolemic rabbit model. New Zealand white male rabbits were placed on a 1% cholesterol diet with (n=5) and without (n=5) 200 µg/mL apocynin added to their drinking water. After one month from commencement of feed, animals were infused with horseradish peroxidase (HRP) as a permeability tracer one minute prior to sacrifice. The aortas were excised, opened, and pinned to a dissecting tray. Gross visual inspection revealed that aortas of 1% cholesterol-fed rabbits without apocynin treatment had typical, diffuse early atherosclerotic lesions. In contrast, an absence of lesions was noted in the aortas of hypercholesterolemic rabbits treated with apocynin. Subsequently, aortas were exposed to diaminobenzidine and $H_2O_2$, and a brown reaction precipitate developed at sites of high HRP concentrations. Aortas of hypercholesterolemic rabbits without apocynin treatment had marked, diffuse areas of high HRP concentrations. However, aortas of hypercholesterolemic animals treated with apocynin consistently showed few HRP-positive areas, a pattern similar to that seen in rabbits fed standard rabbit chow. The total serum cholesterol levels of hypercholesterolemic rabbits with and without apocynin treatment were comparable.

A three month study was also carried out using ten New Zealand white male rabbits fed a 1% cholesterol diet with 30 µg/mL (n=2), 200 µg/mL (n=2), 400 µg/mL (n=2), 800 µg/mL (n=2), and without (n=2) apocynin added to their drinking water. After three months, the animals were sacrificed, and their aortas were examined as before. Visual inspection revealed that aortas of 1% cholesterol-fed rabbits without apocynin treatment had in the range of 60% of aortic surface area covered with atherosclerotic plaque. In contrast, a dose-dependent diminution of lesions was noted in the aortas of hypercholesterolemic rabbits treated with apocynin. In animals treated with greater than 200 µg/mL of apocynin, aortic surface covered with plaque was reduced to less than 8%. The total serum cholesterol levels of hypercholesterolemic rabbits with and without apocynin treatment were comparable at about 1000 mg/dL.

Figure 4:
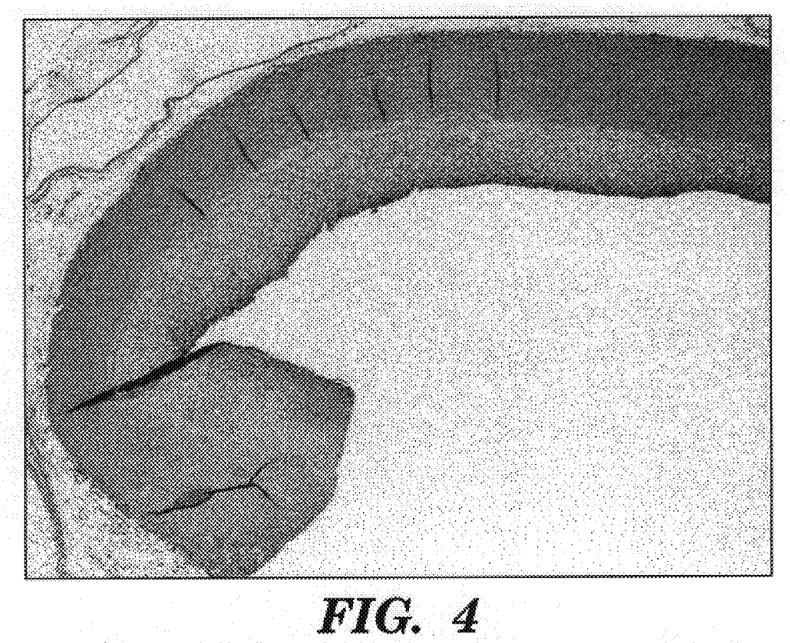
FIG. 4 is a printed reproduction of a photomicrograph of a section of abdominal aorta from a rabbit fed a high cholesterol diet.
Figure 5:
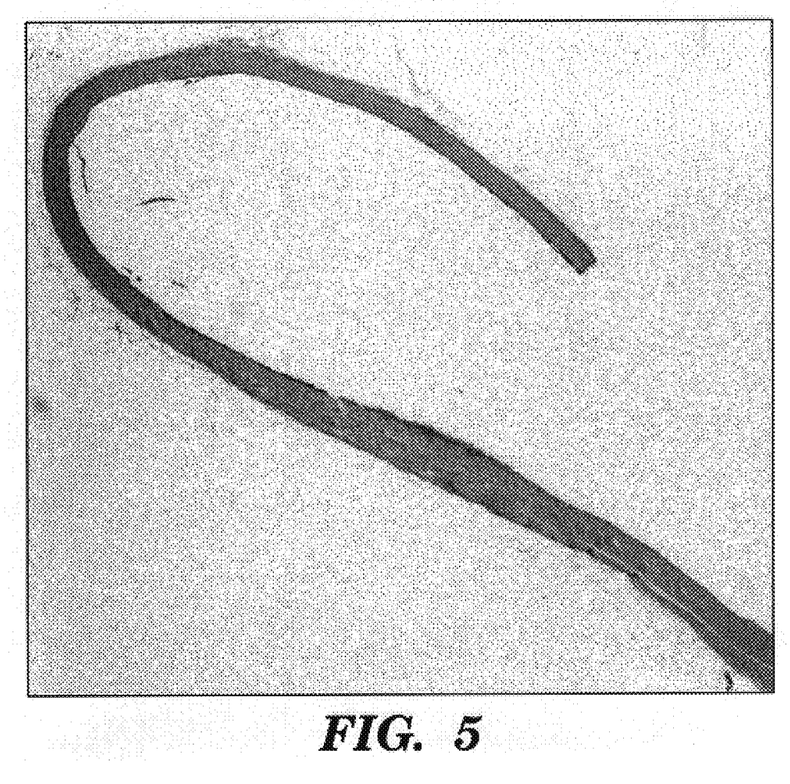
FIG. 5 is a printed reproduction of a photomicrograph of a section of abdominal aorta from a rabbit fed a high cholesterol diet and also given apocynin according to the invention.

Morphologic examination of aortic endothelium from the one and three-month rabbits was performed. Random tissue samples were taken from the thoracic and abdominal aortas of hypercholesterolemic rabbits and hypercholesterolemic rabbits treated with apocynin. Tissue samples were thin sectioned and processed for microscopy. Examination of electron and light micrographs from hypercholesterolemic rabbits without apocynin treatment revealed frequent and diffuse vascular changes characteristic of atherosclerotic disease. FIG. 4 is a representative light micrograph. In contrast, examination of multiple tissue samples from hypercholesterolemic rabbits with apocynin treatment revealed little evidence for vascular changes. FIG. 5 is a representative light micrograph. The effect of NADPH oxidase inhibition on coronary artery endothelium was similarly examined. Like the abdominal aorta, the coronary artery was found to exhibit vascular changes characteristic of atherosclerotic disease, and these changes were attenuated by treatment with apocynin.

To provide experimental evidence that apocynin reduces vascular hyperpermeability by preventing heightened EC endocytosis from occurring, the number of endocytotic vesicles on EC luminal and abluminal sides from electron micrographs were counted as an approximate measure of endocytotic activity. Electron micrographs of 50 randomly selected cells from aortas of hypercholesterolemic rabbits treated with and without apocynin were taken at 35,000× magnification. Endocytotic vesicles were counted on luminal and abluminal cell sides. Vesicles counted included those that were forming in the plasma membrane or clearly attached to the membrane. A significant decrease in the number of endocytotic vesicles in apocynin treated animals was observed, suggesting that apocynin acts by averting endocytosis increases.

Side Effects

Rabbits treated with apocynin for a three month period demonstrated no overt signs of ill health. Weight gain, over the three month period, for apocynin-treated rabbits was comparable to those animals without apocynin treatment.

One might have expected that apocynin might increase susceptibility to infections, since white blood cells use NADPH oxidase to generate ROS to kill bacteria. However, no increased incidence of infections in the New Zealand White male rabbits was seen.

Another theoretical side effect of apocynin might have been thought to result from inhibition of cell proliferation. Certain tissues of the body, including bone marrow and gastrointestinal cells, have higher cell proliferation rates. Cell growth studies showed the dose-dependent effect of apocynin on endothelial and smooth muscle cell proliferation. At 100 µg/mL apocynin, the cell proliferation rates were minimal, however, visual inspection of the cells revealed no evidence of cell injury or death at the apocynin concentrations tested. Thus, at concentrations that inhibit ROS generation, apocynin is highly effective at suppressing cell proliferation.

Conclusion

The above studies in vitro and in vivo indicate that the administration of NADPH oxidase inhibitors, such as apocynin, can prevent and treat diseases associated with hyperpermeability of endothelial cells, including atherosclerosis and its related diseases. In addition to the prevention of atherosclerosis, NADPH oxidase inhibitors, such as apocynin, may be useful for the prevention and treatment of the following conditions by decreasing membrane permeability and cell proliferation associated therewith: arthritis, cancer, sepsis; post-stroke and post-MI tissue swelling and reperfusion injury; adult respiratory distress syndrome (ARDS); growth malignancies; post-transplant vascular changes; vasculitides; asthma and diabetes mellitus.

The optimal dose of the NADPH oxidase inhibitor, such as apocynin, to be used in humans will vary depending upon the severity and nature of the condition to be treated, the route of administration, the age, weight, and sex of the patient, as well as on any other medications being taken by the particular patient or the existence of any complicating significant medical conditions of the patient being treated. The dose and perhaps the dose frequency will also vary according to the response of the individual patient. In general, the total daily dose range for apocynin for the conditions described herein is from about 10 mg/kg/day to about 45 mg/kg/day; for the average human, the total dose is about 500 mg to about 3000 mg daily, preferably in divided doses. In managing the patient, the therapy should be initiated at a lower dose, perhaps at about 200 mg to about 500 mg, and increased up to about 1000 mg depending on the patient's global response. It is further recommended that patients over 65 years and those with impaired renal or hepatic function initially receive low doses and that they be titrated based on individual response(s) and blood level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to prevent" a condition are encompassed by the above-described dosage amounts and dose frequency schedule.

Any suitable route of administration may be employed for providing the patient with an effective dosage of apocynin. For example, oral, rectal, parenteral (subcutaneous, intramuscular, intravenous), transdermal, aerosol and like forms of administration may be employed. Oral dosage is preferred.

Studies on Prediction of Risk of Atherosclerosis

If a heightened endocytosis mechanism predominantly involves an endothelial cell defect rather than an atherogenic LDL type, one could explain why certain people with plasma LDL levels commonly associated with atherosclerosis do not develop atherosclerotic-related diseases. The EC defect hypothesis would also suggest that atherosclerotic patients should exhibit in common some elevation in NADPH oxidase activity.

To test the hypothesis, 92 high LDL-EC endocytosis experiments with cell isolates from 92 separate human umbilical cords were conducted in vitro. In addition, LDL preparations, isolated weekly from different human sources, were generally used on EC isolates derived from two or more human sources, thus allowing for analysis of LDL's effect. Endothelial cells from the same cord all had similar endocytotic activity with exposure to high LDL levels. In contrast, EC from different cord sources responded differently, ranging from no endocytosis change to 200–300% increases in endocytotic activity over control cells.

In 52% of EC isolates tested, high LDL exposure induced a wide variation in degree of response ranging from 5 to 300% endocytosis increases. This observation in vitro correlates with epidemiologic studies that indicate that mortality from atherosclerotic-related diseases occurs in approximately 50% of the population.

If, contrary to the EC hypothesis, an atherogenic LDL type exists, one would expect that EC isolates from multiple human sources would all have similar responses when exposed to the same LDL preparation. EC isolates tested were classified as no response (0 to 5% endocytosis increase) or response (5 to 300% endocytosis increase) and analyzed. Results showed that in only 53% of experiments did all EC isolates, exposed to the same LDL preparation, either respond or have no response. The importance of this finding is that it suggests the likelihood that the heightened endocytosis mechanism predominantly involves an EC defect rather than an atherogenic LDL type. Thus, high levels of LDL's appear to activate the heightened endocytosis mechanism.

This finding explains why certain people with plasma LDL levels commonly associated with atherosclerosis do not develop atherosclerotic-related diseases and leads to the inventive method for predicting an individual's risk of atherosclerosis. By identifying a patient having elevated NADPH oxidase activity, one can predict an increased risk of atherosclerosis. Administration of apocynin or other NADPH oxidase inhibitor can then be recommended for preventing atherosclerosis and its related diseases to those identified patients.

If genetic variants of NADPH oxidase or enzymes involved in its activation exist in the human population, and some of these variants generate excessive amounts of reactive oxygen species, this should correlate with clinical atherosclerosis. Human studies were therefore undertaken. In theses studies, the polymorphonuclear leukocyte (PMN) NADPH oxidase activity in individuals having a history of clinically documented atherosclerosis-related diseases or strong family history thereof was compared with that of individuals having no medical or family history of the diseases. Volunteers provided a medical and family history of atherosclerotic related diseases and a venous blood sample. PMN NADPH oxidase activity was measured by flow cytometry with a fluorescent probe, using 2,7-dichlorofluorescin diacetate as indicator. NADPH oxidase activity was determined by taking fluorescent measurements from the PMN gated window. For these studies, 22 individuals with either clinically documented medical or family history of atherosclerotic-related diseases (experimental) were compared to 11 individuals (controls) with no clinical evidence of or family history of the diseases.

Figure 6:
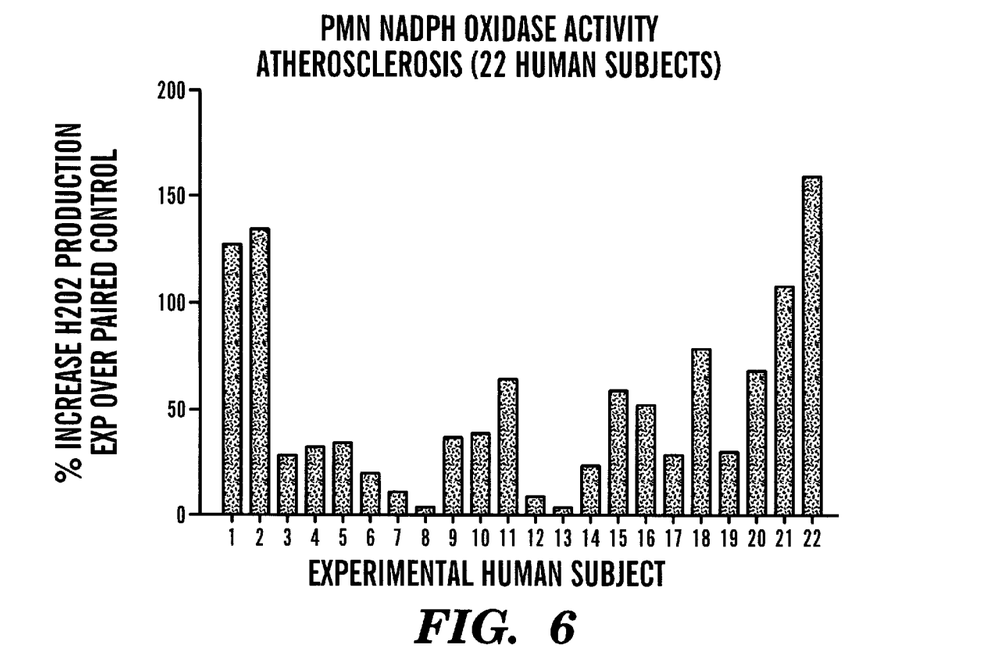
FIG. 6 is a bar graph showing the percent increase in $H_2O_2$ production (i.e. elevation of oxidase activity) for each of 22 patients with a family history of atherosclerosis compared to a paired control.

The results, as illustrated in FIG. 6, reveal that the 22 experimental human subjects had significantly increased NADPH oxidase activity over their paired controls (Probability for significance of test: $P<0.07$). The findings suggest that genetic variants of NADPH oxidase (or enzymes involved in its activation) exist, and that people with these genetic variants are at higher risk of atherosclerotic-related diseases.

While the invention has been particularly shown and described with reference to preferred embodiments thereof, it will be understood by those skilled in the art that other changes in form and details may be made therein without departing from the spirit and scope of the invention.

We claim:

1. A method of treating a condition resulting from endothelial hyperpermeability which comprises administering to a mammal suffering from a condition resulting from endothelial hyperpermeability a therapeutically effective amount of an NADPH oxidase inhibitor or a metabolic precursor of an NADPH oxidase inhibitor, said therapeutically effective amount of said NADPH oxidase inhibitor or precursor being insufficient to lower serum LDL by more than 10%.

2. A method of treating a condition resulting from endothelial hyperpermeability which comprises administering to a mammal suffering from a condition resulting from endothelial hyperpermeability a therapeutically effective amount of an NADPH oxidase inhibitor or a metabolic precursor of an NADPH oxidase inhibitor, said NADPH oxidase inhibitor or precursor having a lower $IC_{50}$ vs human NADPH oxidase than vs human HMG-CoA reductase.

3. A method of treating a condition resulting from endothelial hyperpermeability which comprises administering to a mammal suffering from a condition resulting from endothelial hyperpermeability a therapeutically effective amount of an NADPH oxidase inhibitor or a metabolic precursor of an NADPH oxidase inhibitor, said NADPH oxidase inhibitor or precursor effecting statistically equivalent inhibition of human NADPH oxidase in the presence and absence of mevalonate.

4. A method of preventing a condition resulting from endothelial hyperpermeability which comprises administering to a mammal a therapeutically effective amount of an NADPH oxidase inhibitor or a metabolic precursor of an NADPH oxidase inhibitor, said therapeutically effective amount of said NADPH oxidase inhibitor or precursor being insufficient to lower serum LDL by more than 10% but sufficient to prevent said condition resulting from endothelial hyperpermeability.

5. A method of preventing a condition resulting from endothelial hyperpermeability which comprises administering to a mammal an amount of an NADPH oxidase inhibitor or a metabolic precursor of an NADPH oxidase inhibitor sufficient to prevent said condition resulting from endothelial hyperpermeability, said NADPH oxidase inhibitor or precursor having a lower $IC_{50}$ vs human NADPH oxidase than vs human HMG-CoA reductase.

6. A method of preventing a condition resulting from endothelial hyperpermeability which comprises administering to a mammal an amount of an NADPH oxidase inhibitor or a metabolic precursor of an NADPH oxidase inhibitor sufficient to prevent said condition resulting from endothelial hyperpermeability, said NADPH oxidase inhibitor or precursor effecting statistically equivalent inhibition of human NADPH oxidase in the presence and absence of mevalonate.

7. A method of treating or preventing a condition resulting from endothelial hyper-permeability which comprises administering to a mammal a therapeutically effective amount of a substance which inhibits $p47_{[phox]}$ translocation to the $gp91_{[phox]}$ and $p22_{[phox]}$ membrane bound NADPH oxidase components.

8. The method according to any of claims 1 to 6 wherein said NADPH oxidase inhibitor or precursor is a compound of the formula:

wherein $R^1$, $R^2$ and $R^3$ are independently chosen from the group consisting of H, alkyl, cycloalkyl, heterocycloalkyl, alkenyl, alkynyl, aryl, heteroaryl, arylalkyl, heteroarylalkyl and substituted alkyl, cycloalkyl, heterocycloalkyl, alkenyl and alkynyl.

9. The method according to claim 8 wherein $R^1$ and $R^2$ are each methyl and $R^3$ is H.

10. The method according to any of claims 1 to 6 wherein said NADPH oxidase inhibitor or precursor is a compound of the formula:

or a tautomer thereof, wherein $R^1$, $R^2$ and $R^3$ are independently chosen from the group consisting of H, alkyl, cycloalkyl, heterocycloalkyl, alkenyl, alkynyl, aryl, heteroaryl, arylalkyl, heteroarylalkyl and substituted alkyl, cycloalkyl, heterocycloalkyl, alkenyl and alkynyl.

11. The method according to claim 10 wherein $R^1$ and $R^2$ are each methyl and $R^3$ is H.

12. The method according to any of claims 1 to 7 wherein said condition is atherosclerosis.

13. The method according to claim 12 wherein said NADPH oxidase inhibitor or precursor is a compound of the formula:

wherein $R^1$, $R^2$ and $R^3$ are independently chosen from the group consisting of H, alkyl, cycloalkyl, heterocycloalkyl, alkenyl, alkynyl, aryl, heteroaryl, arylalkyl, heteroarylalkyl and substituted alkyl, cycloalkyl, heterocycloalkyl, alkenyl and alkynyl.

14. The method according to claim 13 wherein $R^1$ and $R^2$ are each methyl and $R^3$ is H.

15. The method according to claim 12 wherein said NADPH oxidase inhibitor is a compound of the formula:

-continued

III or a tautomer thereof, wherein $R^1$, $R^2$ and $R^3$ are independently chosen from the group consisting of H, alkyl, cycloalkyl, heterocycloalkyl, alkenyl, alkynyl, aryl, heteroaryl, arylalkyl, heteroarylalkyl and substituted alkyl, cycloalkyl, heterocycloalkyl, alkenyl and alkynyl.

16. The method according to claim 15 wherein $R^1$ and $R^2$ are each methyl and $R^3$ is H.

17. A method for predicting risk of a human patient to a disease that results from endothelial hyperpermeability said method comprising (a) measuring NADPH oxidase activity in said patient, and (b) identifying a patient having NADPH oxidase activity, more than 10% above the range found in paired controls.

18. The method according to claim 17 wherein said disease that results from endothelial hyperpermeability is atherosclerosis.

19. The method according to claim 17 wherein NADPH oxidase activity is measured in polymorphonuclear leukocytes obtained from the blood of said patient.

20. The method according to claim 19 wherein said measuring is accomplished by flow cytometry.

* * * * *

UNITED STATES PATENT AND TRADEMARK OFFICE
CERTIFICATE OF CORRECTION

PATENT NO. : 5,902,831
DATED : May 11, 1999
INVENTOR(S) : Holland et al.

It is certified that error appears in the above-identified patent and that said Letters Patent is hereby corrected as shown below:

ON THE TITLE PAGE:

Item [75] Inventors: Delete "Genesco" and replace with --Geneseo--.

Col. 12, line 1, after "-continued", please insert one (1) line space before continuing structure beginning with "OCH$_3$".

IN THE CLAIMS:

Claim 7, Col. 17, line 39, delete "hyper-permeability" and replace with --hyperpermeability--.

Signed and Sealed this

Twenty-eighth Day of September, 1999

Attest:

Q. TODD DICKINSON

*Attesting Officer*   *Acting Commissioner of Patents and Trademarks*